US012661207B2

(12) United States Patent
Walter et al.

(10) Patent No.: US 12,661,207 B2
(45) Date of Patent: Jun. 23, 2026

(54) METHOD FOR IDENTIFYING MEDICAL DEVICES

(71) Applicant: VYGON, Écouen (FR)

(72) Inventors: Thomas Walter, Rueil Malmaison (FR); Tiphaine Tenailleau, Sannois (FR); Marie Lafoeste, Saint Denis (FR); Emi Dailly, Persan (FR)

(73) Assignee: VYGON, Écouen (FR)

( * ) Notice: Subject to any disclaimer, the term of this patent is extended or adjusted under 35 U.S.C. 154(b) by 281 days.

(21) Appl. No.: 18/561,256

(22) PCT Filed: May 16, 2022

(86) PCT No.: PCT/EP2022/063203
§ 371 (c)(1),
(2) Date: Nov. 15, 2023

(87) PCT Pub. No.: WO2022/243251
PCT Pub. Date: Nov. 24, 2022

(65) Prior Publication Data
US 2024/0242346 A1     Jul. 18, 2024

(30) Foreign Application Priority Data

May 17, 2021     (FR) ...................................... 2105108

(51) Int. Cl.
A61B 90/90          (2016.01)
G06T 7/00          (2017.01)
(Continued)

(52) U.S. Cl.
CPC ............ A61B 90/90 (2016.02); G06T 7/0012 (2013.01); G06V 10/25 (2022.01); G06V 10/44 (2022.01);
(Continued)

(58) Field of Classification Search
CPC ......... A61B 90/90; G06T 7/00; G06T 7/0012; G06T 2207/30021; G06V 10/25;
(Continued)

(56) References Cited

U.S. PATENT DOCUMENTS 9,121,926 B2 *   9/2015   Nair ...................... A61B 8/445
11,238,962 B1 *   2/2022   LaBorde ................ G16H 10/65
(Continued)

FOREIGN PATENT DOCUMENTS

AU          2014208382 A1 *   7/2015    ............. A61B 6/506
CN          111178453 A   *   5/2020    .......... G06F 18/2411
(Continued)

OTHER PUBLICATIONS

Siyambalapitiya, S. D. M. H., et al. "Generate Navigations to Guide and Automate Nasotracheal Intubation Process." 2019 19th International Conference on Advances in ICT for Emerging Regions (ICTer). vol. 250. IEEE, 2019 (Year: 2019).*
(Continued)

*Primary Examiner* — Stephen R Koziol
*Assistant Examiner* — Benedict E Lee
(74) *Attorney, Agent, or Firm* — NIXON & VANDERHYE

(57)          ABSTRACT

A method for identifying medical devices, referred to as medical devices of interest, the method including: collecting images of the outer portions of the medical devices of interest, each image being labeled with an identifier of the medical device of interest, the images collected forming a training image database; training an identification model from the training image database in order to obtain an identification model trained to assign an identifier to a medical device of interest to be identified according to an image of the outer portion of the medical device; c. receiving an image of the outer portion of a medical device of interest
(Continued)

to be identified; assigning, by the trained classification model, of an identifier to the medical device of interest captured on the received image; and characterizing the medical device of interest according to the assigned identifier.

15 Claims, 8 Drawing Sheets

(51) Int. Cl.
    *G06V 10/25*         (2022.01)
    *G06V 10/44*         (2022.01)
    *G16H 30/40*         (2018.01)

(52) U.S. Cl.
    CPC ... *G16H 30/40* (2018.01); *G06T 2207/30021*
                                       (2013.01)

(58) Field of Classification Search
    CPC ........ G06V 10/44; G06V 20/20; G16H 30/40;
                                      A61M 2205/60
    See application file for complete search history.

(56)                References Cited

U.S. PATENT DOCUMENTS

| | | | | |
|---|---|---|---|---|
| 11,801,011 | B2 * | 10/2023 | Reiner | A61M 5/1723 |
| 11,837,355 | B2 * | 12/2023 | Kim | G16H 30/20 |
| 12,295,753 | B2 * | 5/2025 | Yoo | G16H 50/20 |
| 2014/0007956 | A1 * | 1/2014 | Rutty | A61B 6/504 |
| | | | | 137/551 |
| 2015/0046183 | A1 * | 2/2015 | Cireddu | G16H 40/67 |
| | | | | 705/3 |
| 2015/0087969 | A1 * | 3/2015 | Shekhar | A61B 5/0035 |
| | | | | 600/424 |
| 2015/0209114 | A1 | 7/2015 | Burkholz et al. | |
| 2018/0082036 | A1 * | 3/2018 | Hanrahan | G16H 40/63 |
| 2018/0247024 | A1 * | 8/2018 | Divine | G16H 40/20 |
| 2019/0343588 | A1 | 11/2019 | Juergens | |
| 2019/0371474 | A1 * | 12/2019 | Borsic | A61B 34/10 |
| 2021/0059607 | A1 * | 3/2021 | Gormley | A61B 34/32 |
| 2021/0133999 | A1 * | 5/2021 | Fine | G06N 20/00 |
| 2021/0375487 | A1 | 12/2021 | Kuroda | |

FOREIGN PATENT DOCUMENTS

| | | | | |
|---|---|---|---|---|
| EP | 3307136 | A1 | 4/2018 | |
| EP | 3534356 | A1 * | 9/2019 | G09B 23/303 |
| EP | 2934324 | B1 * | 5/2020 | A61B 8/4416 |
| JP | 2005304596 | A * | 11/2005 | |
| JP | 2009279193 | A | 12/2009 | |
| JP | 2019067415 | A | 4/2019 | |
| JP | 2020062372 | A | 4/2020 | |
| JP | 2021071993 | A | 5/2021 | |
| KR | 20210132130 | A * | 11/2021 | G06V 20/44 |
| RU | 2520369 | C2 * | 6/2014 | A61B 34/20 |
| WO | WO-2012154219 | A2 * | 11/2012 | A61N 5/1084 |
| WO | 2015116805 | A1 | 8/2015 | |
| WO | 2016185180 | A1 | 11/2016 | |

OTHER PUBLICATIONS

Jaroonwit Lelachaicharoeanpan, et al., "Classification of Surgical Devices with Artificial Neural Network Approach" 2021 7th International Conference on Engineering, Applied Sciences and Technology (ICEAST), IEEE, Apr. 1, 2021, pp. 154-159 (6 pages).
Search Report for FR Application No. 2105108 dated Nov. 24, 2021, 2 pages.
International Search Report for PCT/EP2022/063203 mailed Aug. 19, 2022, 7 pages.
Written Opinion of the ISA for PCT/EP2022/063203 mailed Aug. 19, 2022, 7 pages.

\* cited by examiner

METHOD FOR IDENTIFYING MEDICAL DEVICES

CROSS-REFERENCE TO RELATED APPLICATIONS

This application is the US national stage of PCT/EP2022/063203, filed May 16, 2022 and designating the United States, which claims the priority of FR 2105108, filed May 17, 2021. The entire contents of each foregoing application are incorporated herein by reference.

BACKGROUND OF THE INVENTION

Field of the Invention

The present invention relates to a method for identifying medical devices. The invention further relates to an associated computer program.

Description of the Related Art

Different medical devices can be used to put a patient on infusion. In general, such devices comprise an inner part intended for being inserted into the patient, e.g. into a vein, an artery, the esophagus (or other part of the digestive system), the cerebrospinal fluid (epidural catheters) or into a subcutaneous device (e.g. implantable chamber), and an outer part visible from the outside and intended for being handled by healthcare personnel, e.g. for the injection of medicinal or nutrition solutions.

However, it is not always easy for healthcare workers to identify the type of a medical device when the device is already implanted in the patient. And yet, an incorrect identification is likely to lead to serious side effects for the patient, due to non-compliance with the conditions of use of the medical device or the injection of an inappropriate substance.

More particularly, such a risk of mix-up is increased in the case of PICC (peripherally inserted central catheter) and Midline catheters (peripheral venous catheter) since such catheters both emerge in a patients' arm. The risks of mix-up are described in particular in the article Letournel C. Gestion du risque de confusion entre PICC Lines et Midlines [Management of the risk of mix-up between PICC Lines and Midlines. J Pharm Clin 2018; 37(1): 19-26 doi: 10.1684/jpc.2017.0374. The mix-up between PICC and Midlines is likely to lead to a risk of injection of veinotoxic drugs through a Midline catheter or a risk of infection if the maximum period of use is not observed.

Furthermore, it appears that the specificities of use, as well as the best practices of use (Recommendations SF2H: Prévention des infections liées aux catheters périphériques vasculaires et sous cutanés. [Guidelines for the prevention of intravascular catheter-related infections] May 2019, Hygiènes Vol XXVII—no. 2; Infusion Therapy Standards of Practice 8th Edition, January/February 2021, Journal of Infusion Nursing, Vol 44, no. 51) of the different medical devices, whether inserted into the body, in contact with the skin, or connected to devices inserted into the body or in contact with the skin, are not always well known to healthcare personnel. Such mix-up is also likely to lead to complications for the patient due to incorrect use of the devices.

There is thus a need for the implementation of means to reduce the risk of incorrect identification, by healthcare personnel, of medical devices borne by a patient, and thereby to reduce the risk of misuse or non-compliance with the best practices for the use of such devices.

SUMMARY OF THE INVENTION

To this end, the subject matter of the present description is a method for identifying medical devices, called medical devices of interest, the medical devices of interest being devices intended for being inserted into the body of a patient or for being brought into contact with the body of a patient, or are devices intended for being connected to devices inserted into or in contact with a patient's body, each medical device of interest having an outer portion outside the patient's body, the method comprising the following steps:

the collection of images of outer parts of medical devices of interest, each image being labeled with an identifier of the medical device of interest from a set of predefined identifiers, the collected images forming a training image database, the collection step being computer-implemented, the training of an identification model from the training image database in order to obtain an identification model trained to assign an identifier, from the set of predefined identifiers, to a medical device of interest to be identified according to an image of the outer part of the medical device, the training step being computer-implemented, the reception of an image of the outer part of a medical device of interest to be identified, the reception step being computer-implemented, the assignment, by the trained classification model, of an identifier to the medical device of interest imaged on the received image, the classification step being computer-implemented, and the characterization of the medical device of interest according to the assigned identifier.

According to other particular embodiments, the method comprises one or more of the following features, taken individually or according to all technically possible combinations:

the method comprises a step of handling the medical device of interest depending on the characterization carried out.

the training image database consists of images of medical devices of interest of at least two different types, the at least two types of medical devices on the images of the training image database being selected from the following types: medical tube, venous catheter, arterial catheter, enteral nutrition catheter, parenteral nutrition catheter, drainage catheter, epidural catheter, systemic catheter, peripheral insertion central venous catheter, called PICC, peripheral venous catheter, called Midline, central venous catheter, called CVC, umbilical catheter, Huber needle, cutaneous securement system for medical tubes, covering dressing, valve, closed system and stopper connected to a hub of a medical tube.

each identifier is associated with data relating to a type of medical device, the characterization step comprising the determination of the type of the medical device of interest imaged on the received image according to the assigned identifier.

each identifier is associated with recommendations for use of the medical device of interest, the characterization step comprising the determination of recommendations for use of the medical device of interest imaged on the received image according to the assigned identifier.

the recommendations for use comprise one or a plurality of the following recommendations:

the first route of medication to be used for the insertion of the medical device of interest, the maximum rate of injection of liquid into the medical device of interest, the maximum fault pressure of the medical device of interest, the frequency of change of a dressing, if any, applied to the medical device of interest, the compatibility of the medical device of interest with other types of medical devices, the compatibility of the medical device of interest with medicinal solutions, and the compatibility of the medical device of interest with pre-defined medical examinations and, where appropriate, the conditions for carrying out the examinations.

each identifier is associated with an Internet link and/or a remote database through which visual support is obtained with regard to the use of the medical device of interest, the characterization step comprising the display of the visual medium corresponding to the Internet link or to the database associated with the assigned identifier, the visual medium being e.g. a video, an image or an article.

each identifier is associated with at least one structural feature of the medical device of interest, the or at least one structural feature being chosen from: the brand name of the medical device of interest, the contact details of the legal manufacturer of the medical device of interest, the material or materials from which the medical device of interest is made, the potential allergenic material(s), if any, from which the medical device of interest is made, the size of the medical device of interest and, when the medical device of interest is a catheter or a medical tube, the diameter and the initial length of the catheter or the medical tube, the number of lumens in the catheter or the medical tube, the dead volume of each lumen of the catheter or of the medical tube, the flow rates, by gravity or by injection, via a pump or an injector of contrast substances, of the catheter or of medical tube, the characterization step comprising the determination of the structural feature (s) of the medical device of interest imaged on the received image according to the assigned identifier.

each medical device of interest has an inner portion connected to the outer portion, the inner portion being a tube or a needle inserted into the patient's body, the outer portion comprising at least one tube and/or a connector to a tube.

the identifier assigned to the medical device of interest is associated with a remote database from which information on the use of the medical device is obtained.

the information on use comprise data defined by the manufacturer and/or data defined by a healthcare professional when using the medical device on a patient.

the method comprises a step of updating the information for use of the medical device for a given patient and/or a given use, the information for use being archived so as to ensure a patient follow-up and/or a traceability of the medical device.

the identifier is associated with information concerning the environmental impact and/or the eco-design of the medical device of interest.

The present description further relates to a computer program product comprising program instructions stored on a computer-readable storage medium, for the execution of a method as described above when the computer program is executed on a computer.

The present description further relates to a readable information medium on which is stored a computer program product such as described hereinabove.

BRIEF DESCRIPTION OF THE DRAWINGS

Other features and advantages of the invention will appear upon reading hereinafter the description of the embodiments of the invention, given only as an example, and making reference to the following drawings.

DETAILED DESCRIPTION

Figure 1:
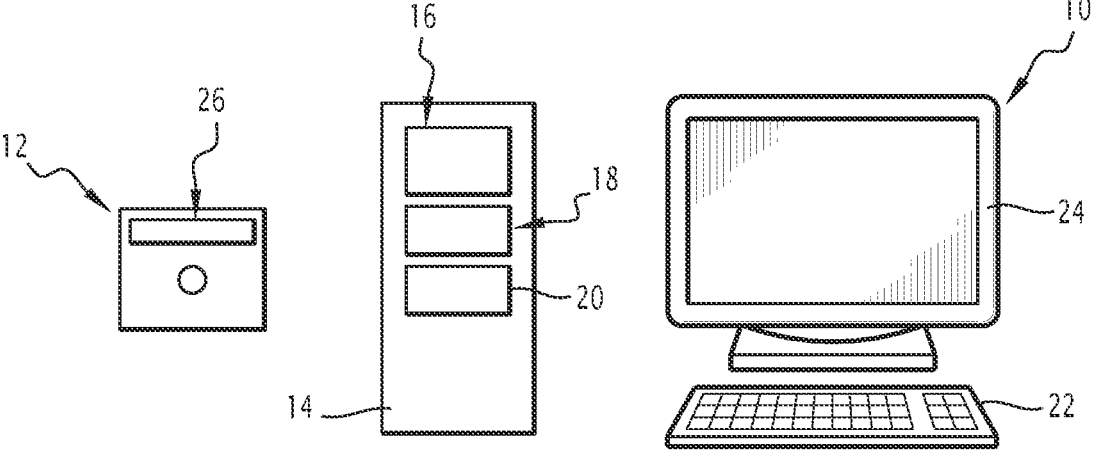
FIG. 1, a schematic view of an example of a computer for implementing a method of identifying medical devices, FIG. 2, a flowchart of an example of implementation of a method of identifying medical devices, FIG. 3, a schematic representation of an example of catheter, FIG. 4, a schematic representation of an example of medical tube, FIG. 5, a schematic representation of an example of a secure Hubber needle, and FIG. 6, a schematic representation of an example of a medical device in contact with a patient's skin (transparent dressing covering the skin insertion site of a catheter), FIG. 7, a schematic representation of another example of a medical device in contact with a patient's skin (catheter placement dressing), and FIG. 8, a schematic representation of an example of a closed system connected to the hub of a catheter.

A calculator 10 and a computer program product 12 are shown in FIG. 1.

The calculator 10 is preferentially a computer.

More generally, the calculator 10 is an electronic calculator suitable for handling and/or transforming data represented as electronic or physical quantities in registers of the calculator 10 and/or memories into other similar data corresponding to physical data in memories, registers or other types of display, transmission or storage.

The calculator 10 interacts with the computer program product 12.

As shown in FIG. 1, the calculator 10 includes a processor 14 comprising a data processing unit 16, memories 18 and a data storage medium 20. In the example illustrated in FIG. 1, the calculator 10 comprises a keyboard 22 and a display unit 24.

The computer program product 12 includes a storage medium 26.

The storage medium 26 is a medium readable by the calculator 10, usually by the data processing unit 16. The readable storage medium 26 is a medium suitable for storing electronic instructions and apt to be coupled to a bus of a computer system.

As an example, the storage medium 26 is a diskette or a floppy disk, an optical disk, a CD-ROM, a magneto-optical disk, a ROM, a RAM, an EPROM, an EEPROM, a magnetic card or an optical card.

The computer program 12 containing program instructions is stored on the storage medium 26.

The computer program 12 can be loaded into the data processing unit 16 and is suitable for leading to the implementation of a method of identifying medical devices when the computer program 12 is implemented on the processing unit 16 of the calculator 10.

Although FIG. 1 illustrates a calculator in the form of a physical computer, the present description is not limited to such a computer type. The description extends to any device integrating a calculator linked to a computer program (computer application).

Thereby, in one embodiment, the calculator and the computer program product 12 are integrated into a smartphone, a touch-sensitive tablet or any other connected object.

Figure 2:
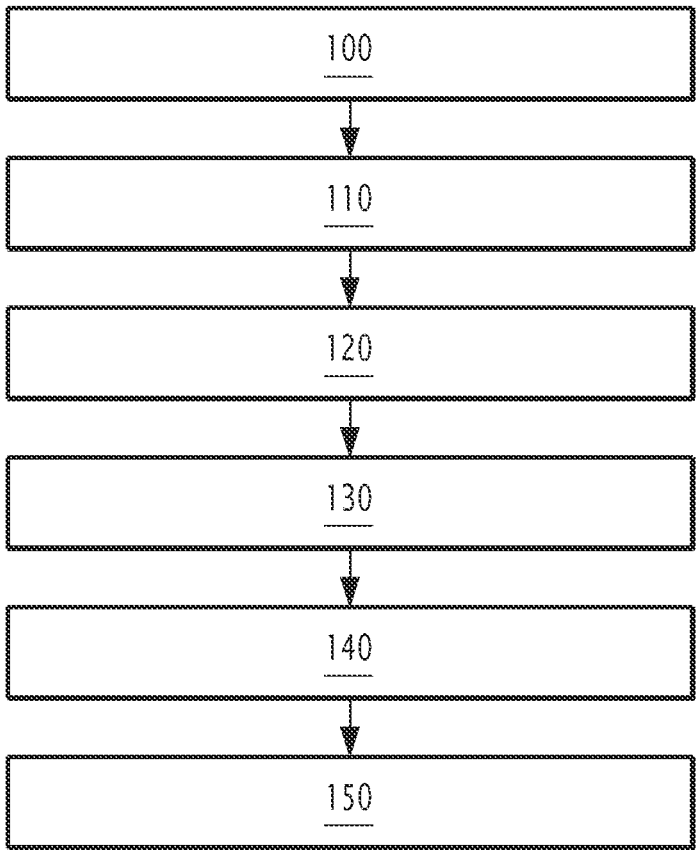

The operation of the calculator 10 will now be described with reference to FIG. 2 which illustrates a flow chart of the implementation of a method of identifying medical devices, and to FIGS. 3 to 8 which illustrate examples of medical devices considered within the framework of the present method.

The medical devices considered within the context of the present method are called medical devices of interest 50.

The medical devices of interest 50 comprise e.g. an inner part 52 and an outer part 54 connected to the inner part 52.

The inner part 52 is intended for being inserted into the body of a patient. When the medical device 50 is already inserted into the body of the patient, the inner part 52 is thus a part which is not visible to the healthcare personnel. The inner part 52 is typically a tube or a needle.

The outer part 54 is intended to remain outside the body of the patient so as to be handled by healthcare personnel, e.g. for the injection of drugs. The outer part 54 comprises at least one tube and/or a tube connector.

Figure 4:
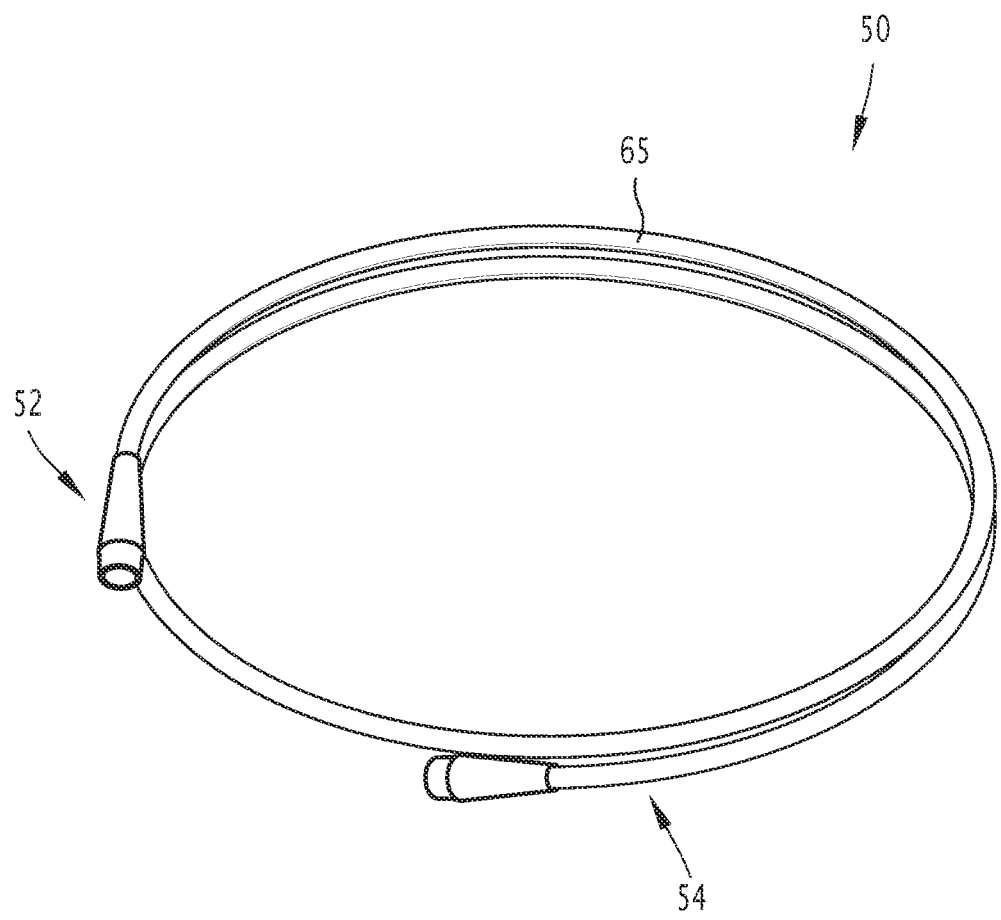
Figure 5:
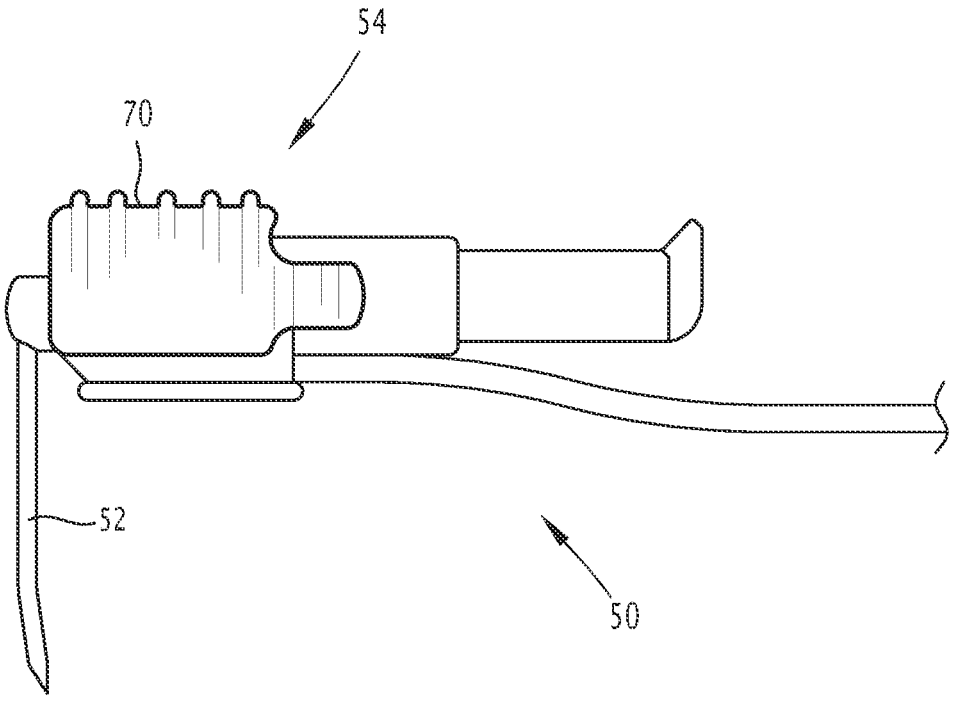

The medical devices of interest 50 considered having an inner part 52 connected to an outer part 54 are e.g. catheters, either tunneled or not tunneled (illustrated in FIG. 3), more widely medical tubes (illustrated in FIG. 4), and/or Huber needles (illustrated in FIG. 5).

Figure 3:
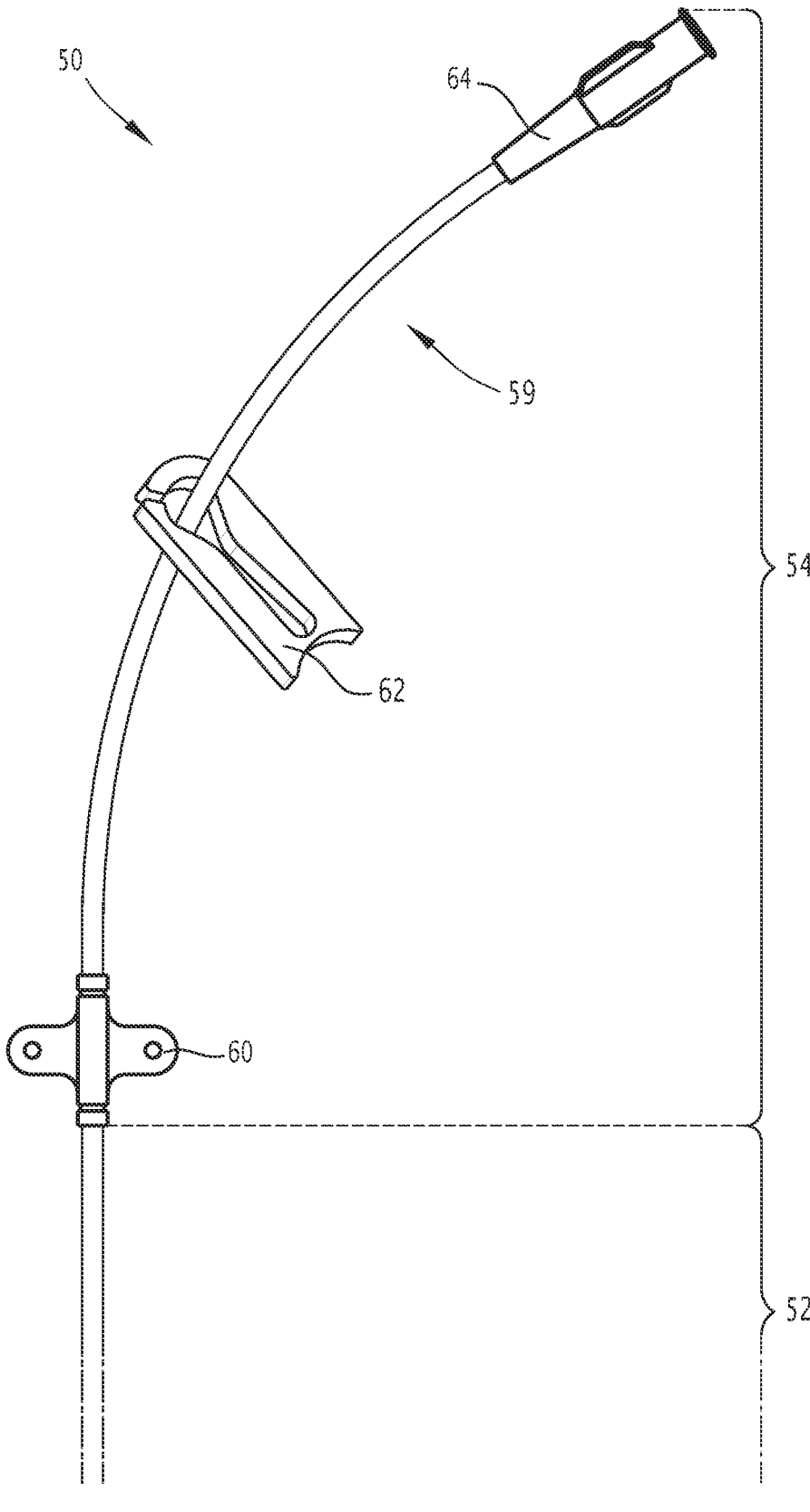

As illustrated in FIG. 3, the outer part 54 of a catheter comprises a tube 59 generally with a hub 60, a clamp 62 and a connector 64 (luer lock). A valve (not shown) is generally inserted at the end of the connector 64. The hub 60 is generally covered with an adhesive or subcutaneous anchor securing system, and a transparent dressing.

The catheters are e.g. venous catheters, arterial catheters, enteral/parenteral nutrition catheters, drainage catheters, epidural catheters, systemic catheters or intravenous catheters. It is clearly established (cf. Outils de Sécurisation et d'auto-evaluation de l'administration des médicaments [Tools for safety and self-assessment of drug administration], HAS, May 2013; ISO 80369-1:2018) that for all such catheters and medical tubes, there are problems related to the mixing up of different routes of approach: in particular central vs peripheral, enteral vs parenteral, pulmonary vs other routes and intrathecal vs intravenous. Multiple routes of medications, as well as the non-recognition of the catheter or medical tube, can be the cause of sometimes serious errors. For example, the injection of vinca alkaloids, which are highly neurotoxic by the intrathecal route of medication, is potentially fatal for the patient. In addition, the injection of molecules classified as vesicants (S. Manrique-Rodriguez, Standardization and Chemical Characterization of intravenous Therapy in Adult Patients: A Step Further in Medication Safety, Drugs in R&D, December 2020) in an unsuitable peripheral catheter may lead to risks of venitis, necrosis or even extravasation.

More specifically, the catheters are e.g. peripherally inserted central venous catheters, called PICCs, peripheral venous catheters, called Midlines, and central venous catheters, called CVCs, central umbilical catheters, or enteral nutrition catheters.

A PICC is a venous catheter intended for being inserted above the bend of the elbow into a deep vein of the arm and going to the cavo-atrial junction. The distal end is thus located at the entrance of the heart. A PICC can be used in particular for the following injections: chemotherapy, antibiotic therapy, parenteral feeding and transfusion. A PICC can remain implanted in a patient for up to 6 months.

A Midline catheter is a catheter intended for being inserted over the bend of the elbow into a vein in the arm and going to the axillary line. The distal end is thus located below the clavicle. A Midline is particularly useful for injections of non-irritant products (<900 mOs/l, 5<pH<9) in prolonged treatment (longer than 8 days), such as antibiotics, analgesics or hydration substances. A Midline can remain implanted in a patient for up to 30 days.

A CVC is a catheter intended for being inserted at the neck, the thorax or at the femur. The distal end of such a catheter is located at the entrance to the heart.

Another type of tube is illustrated by the FIG. 4. In the example illustrated in FIG. 4, the medical device 50 is a tube 65, one end of which is intended for being inserted into the patient and thus forms the inner part 52, and the other end of which forms the outer part 54. In the particular example of FIG. 4, the tube is an oxygen tube. However, the medical device 50 is potentially any other type of tube.

A Huber needle is a device intended for being used on an implantable catheter port, said CCI. The port CCI is a subcutaneous implantable device consisting of an injection reservoir and a central catheter. The Huber needle is used for injections and sampling by puncturing the port housing under the skin. The Huber needle comprises in particular a (tangential bevel) needle to be inserted into the patient's skin at the housing and a connector intended for staying outside so as to be connected e.g. to a tube.

As illustrated in FIG. 5, the inner part 52 of a Huber needle is a (tangential bevel) needle intended for being inserted, at the housing, into the skin of the patient. The outer part 54 comprises a connector 70 intended for staying outside so as to be connected to e.g. a tube.

In addition or in a variant the medical device(s) of interest 50 consist(s) only of an outer part 54 visible from outside the patient (no inner part inserted into the body).

In such case, the outer part 54 is e.g. intended for being in contact with the skin of the patient or for being connected to a medical device intended for being inserted into the body of a patient or in contact with the skin of the patient.

The medical devices of interest 50 considered having only one outer part 54 are e.g. cutaneous systems such as: system for cutaneous securement of medical tubes (catheters, drains, etc.), covering dressing, valves, closed system and plugs connected to the hub of a medical tube (e.g. hub 60 of a catheter).

Figure 6:
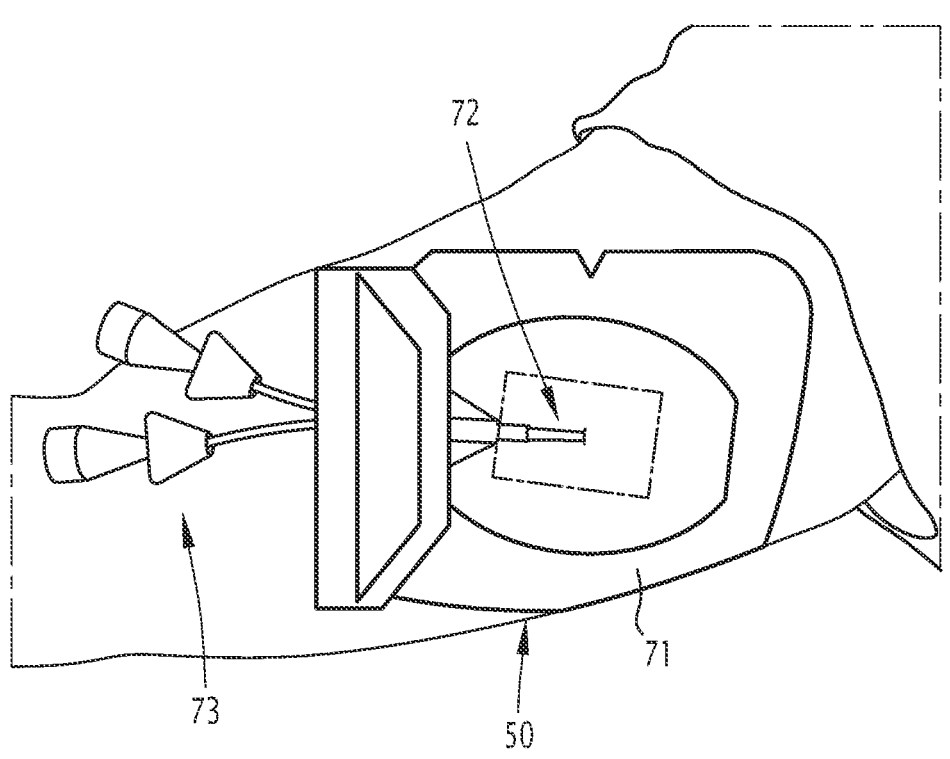

FIG. 6 illustrates, as an example, a medical device of interest 50 in contact with the skin of a patient. In such example, the medical device 50 is a transparent dressing 71 covering the cutaneous insertion site 72 of a catheter 73.

Figure 7:
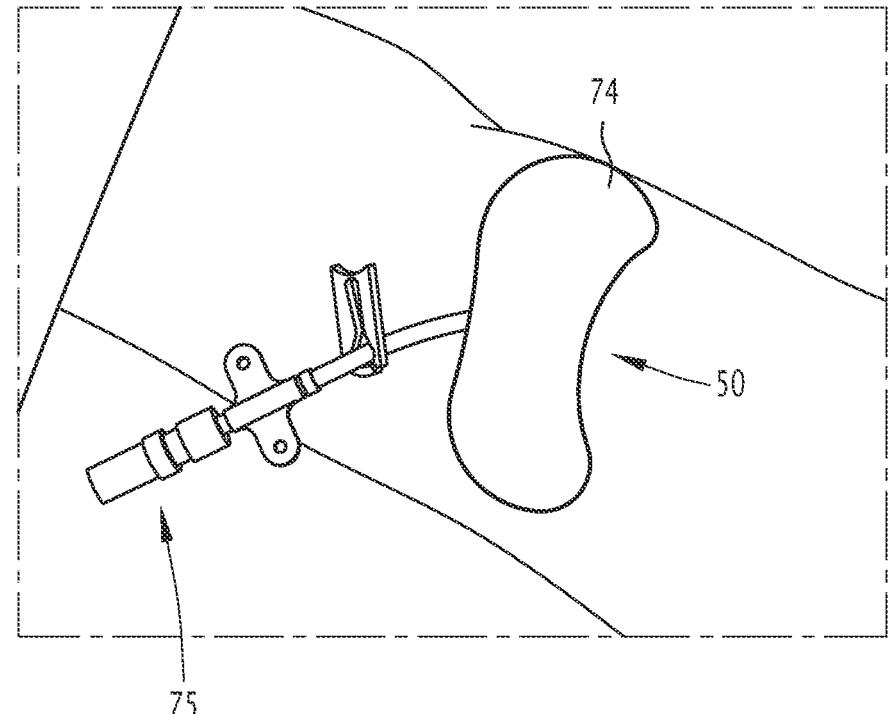

FIG. 7 is another example of a medical device of interest 50 in contact with the skin of a patient. In such example, the medical device 50 is a dressing 74 for securing a catheter 75.

Figure 8:
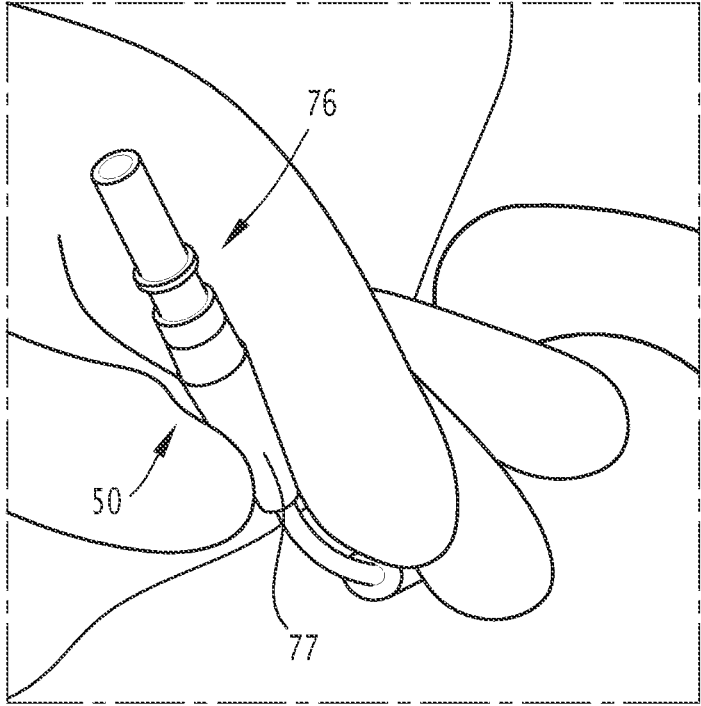

FIG. 8 is yet another example of a medical device of interest 50 connected to a medical device intended for being inserted into the body of a patient or in contact with the skin of the patient. In such example, the medical device 50 is a closed system 76 connected to the hub 77 of a catheter.

The identification method comprises a step 100 of collecting images of outer parts of medical devices of interest 50. Thereby, the collected images form a database of training images. The step 100 is implemented by the calculator 10 in interaction with the computer program product 12, i.e. is computer-implemented.

The images of the database were e.g. acquired by a camera e.g. of a smartphone.

Preferentially, the images collected are images on which the medical devices of interest 50 are in the configuration of use, i.e. that when the devices 50 comprise an inner part 52, the inner part is inserted into the body of the patient, and when the devices 50 comprise only an outer part 54, the outer portion 54 is in contact with the skin of the patient or connected to another medical device inserted into the body or in contact with the skin of the patient. Only the outer parts of the medical devices are thus visible in the images.

In a variant, the collected images also comprise images of medical devices of interest 50 which are not worn by the patient.

The training image database is typically formed by images of medical devices of interest 50 of at least two different types.

In one example, the at least two types of medical devices 50 imaged on the images in the training image database are selected from the following types: medical tube, venous catheter, arterial catheter, enteral nutrition catheter, parenteral nutrition catheter, drainage catheter, epidural catheter, systemic catheter, peripheral insertion central venous catheter, called PICC, peripheral venous catheter, called Midline, central venous catheter, called CVC, umbilical catheter, Huber needle, cutaneous securement system for medical tubes (catheters, drains, etc.), covering dressing, valve, closed system and cap connected to a hub of a medical tube.

In a specific example, at least one type of imaged device is a peripheral insertion central venous catheter, called a PICC, and at least one type of imaged device is a peripheral venous catheter, called Midline, so as to differentiate the two types of catheters.

Each image is labeled with an identifier of the medical device of interest 50 among a set of predefined identifiers. The identifier was e.g. determined by an operator.

Each predefined identifier corresponds to the same category of medical devices, or even to a specific model of medical device (same reference). Medical devices labeled with the same identifier thus have common features or correspond to the same devices.

Advantageously, each identifier is associated with data relating to a type of medical device. The types of medical devices are e.g. one or a plurality of the following types: medical tube, venous catheter, arterial catheter, enteral nutrition catheter, parenteral nutrition catheter, drainage catheter, epidural catheter, systemic catheter, peripheral insertion central venous catheter, called PICC, peripheral venous catheter, called Midline, central venous catheter, called CVC, umbilical catheter, Huber needle, cutaneous securement system for medical tubes (catheters, drains, etc.), covering dressing, valve, closed system and cap connected to a hub of a medical tube.

In a specific example, at least one type of device is a peripheral insertion central venous catheter, called PICC, and at least one type of device is a peripheral venous catheter, called Midline, so as to differentiate the two types of catheters.

Advantageously, each identifier is associated with recommendations for the use of the medical device of interest 50.

The recommendations are intended to guide healthcare personnel in the proper use of the devices.

In one example, the recommendations for use comprise one or a plurality of the following recommendations:
   a. the first route of medication to use (peripheral, central, enteral etc.),
   b. the maximum rate of injection of liquid (by gravity and via a pump or an injector of contrast substance) into the medical device of interest 50,
   c. the maximum fault pressure of the medical device of interest 50,
   d. the frequency of change of a dressing, if any, applied to the medical device of interest 50,
   e. the compatibility of the medical device of interest 50 with other types of medical devices,
   f. the compatibility of the medical device of interest 50 with medicinal solutions, and
   g. the compatibility of the medical device of interest 50 with pre-defined medical examinations and, where appropriate, the conditions for carrying out the examinations.

Advantageously, each identifier is associated with an Internet link and/or a remote database through which a visual medium relating to the use of the medical device of interest 50 is obtained. The visual medium is intended for being viewed or read by healthcare personnel, in order to help with proper handling of the medical device of interest 50. The visual medium is e.g. a video, an image or an article.

Advantageously, each identifier is associated with structural features of the medical device of interest 50. Structural features include, e.g., one or a plurality of the following features: the brand name of the medical device of interest 50, the contact of the legal manufacturer of the medical device of interest 50, the material or materials from which the medical device of interest 50 is made, the potential allergenic material(s), if any, from which the medical device of interest 50 is made, the size of the medical device of interest 50 and, when the medical device of interest 50 is a catheter or a medical tube, the diameter and the initial length of the catheter or the medical tube, the number of lumens in the catheter or the medical tube, the dead volume of each lumen (route) of the catheter or of the medical tube, the flow rates, by gravity or by injection via a pump or an injector of contrast substances, of the catheter or or of the medical tube.

The identification method comprises a step 110 of training an identification model from the training image database. Step 110 is used for obtaining an identification model trained to assign an identifier, among the set of predefined identifiers, to a medical device of interest 50 to be identified, according to an image of the outer part 54 of the medical device of interest 50. The step 100 is implemented by the calculator 10 in interaction with the computer program product 12, i.e. is computer-implemented.

In an example of implementation, the training of the identification model is carried out according to a learning method applied to the database.

The identification model is e.g. a neural network. The learning method model is used for configuring the neural network as the learning thereof progresses on the database. In one example, a part of the database is used for configuring the neural network and the other part for validating the configuration.

Typically, the trained model is apt to first recognize the specific model (reference) of the medical device, corresponding to an identifier, via physical features specific to the device model. Physical features are e.g. the color, the shape or accessories of the medical device. The other features of the device are then found according to the identifier (e.g. the type of the device, the recommendations for use, etc.).

The identification method comprises a step 120 of receiving an image of the outer part 54 of a medical device of interest 50 to be identified. The step 120 is implemented by the calculator 10 in interaction with the computer program product 12, i.e. is computer-implemented.

The imaged medical device of interest 50 is e.g. being used on the patient. In a variant, the imaged medical device of interest 50 is not borne by the patient.

For example, the received image was acquired by the camera of a smartphone. The acquisition was e.g. initiated by healthcare personnel in order to identify a medical device of interest 50, e.g. one or a plurality medical devices of interest 50 inserted into the body of a patient or in contact with the patient's skin.

The identification method comprises a step 130 of assigning, by the trained classification model, an identifier to the medical device of interest 50 imaged on the received image. The classification step is implemented by the calculator 10 in interaction with the computer program product 12, i.e. is computer-implemented.

Advantageously, a probability representative of a confidence level is also determined by identifying same as assigned to the medical device of interest 50. As a result, the healthcare personnel are notified of a potential error in the identification performed. For example, in cases where the probability is below a predetermined threshold (e.g. 85%), it is considered that the identification is potentially erroneous.

The identification method comprises a step 140 of characterizing the medical device of interest 50 according to the assigned identifier. Thereby, at the end of the step 140, at least one feature relating to the medical device of interest 50 imaged on the image received is obtained.

For example, when the identifier is associated with data relating to a type of a medical device, the characterization step 140 comprises the determination the type of the medical device of interest 50 imaged on the image received according to the assigned identifier.

For example, when the identifier is associated with recommendations for use of the medical device of interest 50, the characterization step 140 comprises the determination of recommendations for use of the medical device of interest 50 imaged on the image received according to the assigned identifier.

For example, when the identifier is associated with an Internet link or a remote database, corresponding to a visual support relating to the use of the medical device of interest 50, the characterization step 140 comprises the display of the visual medium corresponding to the Internet link or to the database associated with the assigned identifier.

For example, when the identifier is associated with one or a plurality of structural features, the characterization step 140 comprises the determination of the structural feature or features of the medical device of interest 50 imaged on the received image according to the assigned identifier.

The characterization step 140 is e.g. implemented by the calculator 10 in interaction with the computer program product 12, i.e. is computer-implemented. For example, the features are extracted from a database according to the assigned identifier.

In a variant, the characterization step 140 is implemented by an operator, such as a member of healthcare personnel (replacement of the medical device, injection of substances). The operator will e.g. search a database for features corresponding to the assigned identifier.

In an example of implementation, the identification method comprises a step 150 of handling the medical device of interest 50 according to the characterization carried out. The handling is e.g. performed by an operator, such as member of healthcare personnel.

For example, depending on the characterization performed, the medical device of interest 50 will be handled differently by healthcare personnel. For example, handling and injected substances may differ between a PICC and a Midline catheter.

Thereby, the present method identifies one or a plurality of medical devices from a set of referenced medical devices. Such a method can thus help healthcare personnel identify a device, with a reduced risk of mix-up.

The identification of the medical devices of interest further leads, through the knowledge of the recommendations for use and/or the features of the device identified, to:
    limiting the risks of injection of molecules not suitable for the route of medication of the device,
    following the best practices for the use and maintenance of the device, and
    knowing the incompatibility of the device with other medical devices.

A person skilled in the art will understand that the embodiments and variants described above can be combined so as to form new embodiments provided that same are technically compatible.

More particularly, as a variant or an optional addition to the preceding embodiments, the identifier assigned to the medical device of interest is associated with a remote database through which information on the use of the medical device is obtained. As a result, it is possible to have access to information which is not readily available at the patient's home, or even at the hospital. However, such information is crucial for the safe use of the medical device. More particularly, the following two typical examples could have serious consequences for the patient if the information on use is not known:
    $1^{st}$ example: The maximum injection rate is not observed, leading to the rupture of the catheter, and thereby potential extravasations.
    $2^{nd}$ example: Poor knowledge of the presence of the catheter in the central or peripheral venous network being likely to cause an injection of veinotoxic molecules in the peripheral, destroying the veins of the patient.

Thereby, when the identifier assigned to the medical device of interest is associated with a remote database, the method provides access to such information on use. Information on use is typically manufacturer-specific (guaranteeing proper use) and/or is established/supplemented by healthcare professionals with actual use data. Thus, the information on use is e.g.
    Coming from the manufacturer (maximum flow-rate), i.e. the information is not found by doing an Internet search or in a bibliographic article, specifically and with certainty for the references concerned, and/or
    Coming from the healthcare professionals themselves (central or peripheral).

In an example of implementation, the information on use initially comprise default information, e.g., information relating to a specific feature of the medical device defined by the manufacturer, e.g. central or peripheral. Then, secondly, the information on use is supplemented by the person handling the medical device (healthcare professional) by entering additional information in the database such as: name of the vein first used, length of the implanted catheter, date of implantation, etc. Such additional information thus supplements the information by default. Preferentially, the information on use is also supplemented by any user of the medical device (healthcare professional) by incorporating additional information such as the type of treatment admin- istered, as well as the quality of the injection (absence of pain, redness, etc.) thus ensuring the traceability of the use of the medical device and the safety thereof.

As an optional addition or in a variant, the information on use is archived in a database (in an application or memory) in order to provide follow-up for the patient. For example, once the medical device has been identified, the healthcare professional can return to the application to find the previ- ously explained information on use (manufacturer and his/ her own follow-up). The healthcare professional will be able to find all the medical devices used scanned and the uses thereof, thus ensuring the traceability and safety of his/her actions.

Preferentially, the information on use is suitable for being extracted from said follow-up (e.g. all the catheters placed/ used by an operator) to make therefrom a statistical report which could be used by healthcare professionals e.g. at the medical-legal level or for monitoring clinical activity or for the manufacturer as a post-market monitoring tool (post-CE) under the new MDR regulation. In the latter framework, the goal is to establish a database of the use of medical devices, in particular catheters.

In a variant or as an optional addition, the identifier is associated with information with regard to the environmen- tal impact and/or the eco-design of the medical device of interest. Such information is e.g. released by the manufac- turer. Such information comprises e.g. a rating of the medi- cal device of interest. In particular, such information com- prises e.g. one or a plurality of the following data: the carbon impact, any admixtures included in the composition of the medical device of interest, and information with regard to the recycling (packaging) of the medical device of interest.

The invention claimed is:

1. A method of identifying medical devices, called medi- cal devices of interest, the medical devices of interest being i) devices intended for being inserted into a patient's body, ii) devices intended for being brought into contact with the patient's body, and iii) devices intended for being connected to devices inserted into or in contact with the patient's body, each medical device of interest having an outer part visible from outside the patient's body, the method comprising the following steps:

a. collection of images of the outer parts of medical devices of interest, each image being labeled with an identifier of the medical device of interest from a set of predefined identifiers, the collected images forming a training image database, the collection of images being computer-implemented, b. training of an identification model from the training image database in order to obtain an identification model trained to assign an identifier, from the set of predefined identifiers, to a medical device of interest to be identified according to an image of the outer part of the medical device, the training of the identification model to be a trained identification model being com- puter-implemented, c. obtaining a received image by reception of an image of the outer part of a medical device of interest to be identified, the reception of the image being computer- implemented, d. assignment, by a trained classification model, of an identifier to the medical device of interest imaged on the received image, the assignment by the trained classification model being computer-implemented, and e. characterizing the medical device of interest according to the assigned identifier, wherein each identifier is associated with at least one of an Internet link and a remote database through which visual support is obtained with regard to the use of the medical device of interest, the characterization step comprising a display of the visual medium correspond- ing to the Internet link or to a database associated with the assigned identifier.

2. The method according to claim 1, wherein the method comprises a step of handling the medical device of interest according to the step of the characterizing the medical device of interest according to the assigned identifier.

3. The method according to claim 1, the training image database consisting of images of medical devices of interest of at least two different types, the at least two types of medical devices being selected from: medical tube, venous catheter, arterial catheter, enteral nutrition catheter, paren- teral nutrition catheter, drainage catheter, epidural catheter, systemic catheter, peripheral insertion central venous cath- eter, called PICC, peripheral venous catheter, called Mid- line, central venous catheter, called CVC, umbilical catheter, Huber needle, cutaneous securement system for medical tubes, covering dressing, valve, closed system and stopper connected to a hub of a medical tube.

4. The method according to claim 1, wherein each iden- tifier is associated with data relating to a type of medical device of interest, the characterization step comprising determination of the type of the medical device of interest imaged on the received image according to the assigned identifier.

5. The method according to claim 1, wherein each iden- tifier is associated with recommendations for use of the medical device of interest, the characterization step com- prising determination of recommendations for use of the medical device of interest imaged on the received image according to the assigned identifier.

6. The method according to claim 5, wherein the recom- mendations for use comprises one or a plurality of the following recommendations:

a. a first route of medication to be used for insertion of the medical device of interest, b. a maximum rate of injection of liquid into the medical device of interest, c. a maximum fault pressure of the medical device of interest, d. a frequency of change of a dressing, if any, applied to the medical device of interest, e. a compatibility of the medical device of interest with other types of medical devices, f. a compatibility of the medical device of interest with medicinal solutions, and g. a compatibility of the medical device of interest with pre-defined medical examinations and, where appro- priate, the conditions for carrying out the examinations.

7. The method according to claim 1, wherein each iden- tifier is associated with at least one structural feature of the medical device of interest, the or at least one structural feature being chosen from: a brand name of the medical device of interest, contact details of the legal manufacturer of the medical device of interest, a material or materials from which the medical device of interest is made, a potential allergenic material(s), if any, from which the medical device of interest is made, a size of the medical device of interest and, when the medical device of interest is a catheter or a medical tube, a diameter and an initial length of the catheter or the medical tube, a number of lumens in the catheter or the medical tube, a dead volume of each lumen of the catheter or of the medical tube, flow rates, by gravity or by injection, via a pump or an injector of contrast substances, of the catheter or of the medical tube, the characterization step comprising the determination of the structural feature(s) of the medical device of interest imaged on the received image according to the assigned identifier.

8. The method according to claim 1, wherein each medical device of interest has an inner portion connected to the outer part, the inner portion being a tube or a needle inserted into the patient's body, the outer part comprising at least one tube or a connector to a tube.

9. The method according to claim 1, wherein the identifier assigned to the medical device of interest is associated with a remote database from which information on use of the medical device is obtained.

10. The method according to claim 9, wherein the information on use comprise at least one of data defined by manufacturer and data defined by a healthcare professional when using the medical device on a patient.

11. The method according to claim 9, wherein the method comprises a step of updating the information for at least one of use of the medical device for a given patient and a given use, the information for use being archived so as to ensure at least one of a patient follow-up and a traceability of the medical device.

12. The method according to claim 1, wherein the identifier is associated with information with regard to at least one of the environmental impact and an eco-design of the medical device of interest.

13. A computer-readable storage medium on which are stored program instructions that implement the steps of the identification method according to claim 1 when the computer program is executed on a computer.

14. The method according to claim 1, wherein the outer part of each medical device of interest is configured for remaining outside of the patient's body for being handled by healthcare personnel.

15. The method according to claim 1, wherein the outer part of each medical device of interest is configured for remaining outside of the patient's body for injection of solutions into the patient's body.

* * * * *